United States Patent
Yokomaku et al.

(10) Patent No.: US 7,282,520 B2
(45) Date of Patent: Oct. 16, 2007

(54) EXTERNAL PREPARATION

(75) Inventors: Atsushi Yokomaku, Tokyo (JP); Taketoshi Ito, Tokyo (JP); Megumi Aono, Tokyo (JP); Shinichi Watanabe, Tokyo (JP); Yuichi Nishida, Tokyo (JP)

(73) Assignee: Lion Corporation, Tokyo (JP)

( * ) Notice: Subject to any disclaimer, the term of this patent is extended or adjusted under 35 U.S.C. 154(b) by 147 days.

(21) Appl. No.: 10/489,910

(22) PCT Filed: Sep. 13, 2002

(86) PCT No.: PCT/JP02/09457

§ 371 (c)(1), (2), (4) Date: Mar. 18, 2004

(87) PCT Pub. No.: WO03/026598

PCT Pub. Date: Apr. 3, 2003

(65) Prior Publication Data
US 2004/0247551 A1    Dec. 9, 2004

(51) Int. Cl.
*A61K 31/235* (2006.01)
(52) U.S. Cl. .................. 514/532; 514/844; 514/881
(58) Field of Classification Search ............... 514/844, 514/881, 532
See application file for complete search history.

(56) References Cited

FOREIGN PATENT DOCUMENTS

| | | |
|---|---|---|
| EP | 0 649 648 A2 | 4/1995 |
| JP | 62-215512 A | 9/1987 |
| JP | 04-273811 A | 9/1992 |
| JP | 05-124921 A | 5/1993 |
| JP | 05-125392 A | 5/1993 |
| JP | 06-032724 A | 2/1994 |
| JP | 6-40864 A | 2/1994 |
| JP | 06-345620 A | 12/1994 |
| JP | 7-173046 A | 7/1995 |
| JP | 07-258044 A | 10/1995 |
| JP | 07-285836 A | 10/1995 |
| JP | 07-316024 A | 12/1995 |
| JP | 08-012993 A | 1/1996 |
| JP | 08-143432 A | 6/1996 |
| JP | 08-310922 A | 11/1996 |
| JP | 09-124437 A | 5/1997 |
| JP | 09-157140 A | 6/1997 |
| JP | 2000-319116 A | 11/2000 |

*Primary Examiner*—Taofiq Solola
(74) *Attorney, Agent, or Firm*—Birch, Stewart, Kolasch & Birch, LLP

(57) ABSTRACT

An external preparation characterized by comprising, as selected from gallic acid derivatives of the following formula (I),

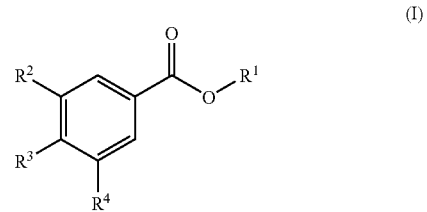

(I)

wherein $R^1$ represents a hydrogen atom, an alkali metal, an alkaline earth metal, an ammonium salt, or an alkyl or alkenyl group having from 1 to 18 carbon atoms and $R^2$, $R^3$, and $R^4$ independently represent a hydrogen atom, an hydroxyl group, an alkoxy group having from 1 to 18 carbon atoms, a polyoxyethylene group, a polyoxypropylene group, or a residue of a monosaccharide, a disaccharide, or an oligosaccharide; 90 wt % or over of one or more gallic acid derivatives (A) wherein two of $R^2$, $R^3$, and $R^4$ in the formula (I) independently represent a residue of a monosaccharide, disaccharide, or oligosaccharide and from 0.001 wt % to less than 10 wt % of one or more gallic acid derivatives (B) wherein one of $R^2$, $R^3$, and $R^4$ represents a residue of a monosaccharide, disaccharide, or oligosaccharide, each based on the total content of the gallic acid derivatives.

5 Claims, No Drawings

EXTERNAL PREPARATION

TECHNICAL FIELD

This invention relates to a preparation for external use formulated with a gallic acid glucoside, and more particularly, to a preparation for external use that is applicable as a hair cosmetic wherein the gallic acid glucoside is suppressed from being precipitated and settled at low temperatures.

BACKGROUND ART

It is known that gallic acid and ester products thereof have the capabilities of skin whitening, antioxidation, impartment of stiffness and elasticity to hair and remedy of the hair damaged through coloring or by the action of a perm agent (remedy of F-layer and microfibrils). In fact, such a preparation has been expected for applications in various fields such as skin preparations for external use in the form of a cream or an emulsion, hair treatments such as hair styling agents or gels, and the like. However, gallic acid and its esters are usually poor in stability. In the course of actual preparation, a problem, which is coloration or precipitation, makes it difficult to show the functions or capabilities satisfactorily. In addition, some types of gallic acid esters are substantially insoluble in water, with the possibility that limitation is placed on the amount used.

In order to solve these problems, glucosylation of gallic acid and esters thereof wherein a saccharide is joined to the phenolic hydroxyl groups of gallic acid has been proposed (Japanese Patent Laid-open No. 2000-319116). Although such gallic acid glucosides are improved in solubility at normal temperatures, the solubility at low temperatures is so low that a problem arises in that when a solution of a gallic acid glucoside in water or a mixed solvent of water/polar organic solvent is allowed to stand at low temperatures, a precipitate is formed.

As described above, gallic acid glucosides are low in solubility in water or a mixed solvent of water/polar organic solvent at low temperatures, with the attendant problem that a precipitate settles.

DISCLOSURE OF INVENTION

An object of the invention is to provide a preparation for external use wherein gallic acid glucosides are suppressed from precipitating at low temperatures.

In order to achieve the above object, the present inventors have made intensive studies on gallic acid glucosides being suppressed from precipitating at low temperatures and, as a result, found that an external preparation having excellent low temperature stability is obtained by formulating gallic acid derivatives (A) and (B) of the following formula in the specific amounts, and preferably further formulating a cationic surface active agent. The invention has been accomplished based on the above finding.

The invention provides an external preparation, which is characterized by including, as selected from gallic acid derivatives of the following formula (I),

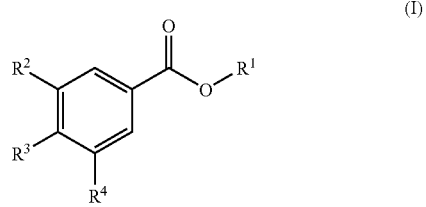

wherein $R^1$ represents a hydrogen atom, an alkali metal, an alkaline earth metal, an ammonium salt, or an alkyl or alkenyl group having from 1 to 18 carbon atoms; $R^2$, $R^3$, and $R^4$ independently represent a hydrogen atom, an hydroxyl group, an alkoxy group having from 1 to 18 carbon atoms, a polyoxyethylene group, a polyoxypropylene group, or a residue of a monosaccharide, a disaccharide or an oligosaccharide; 90 wt % or over of one or more gallic acid derivatives (A) wherein two of $R^2$, $R^3$, and $R^4$ in the formula (I) independently represent a residue of a monosaccharide, disaccharide, or oligosaccharide; from 0.001 wt % to less than 10 wt % of one or more gallic acid derivatives (B) wherein one of $R^2$, $R^3$ and $R^4$ represents a residue of a monosaccharide, disaccharide, or oligosaccharide, each based on the total content of the gallic acid derivatives.

BEST MODE FOR CARRYING OUT THE INVENTION

The external preparation of the invention is suitably used, particularly, as hair cosmetics. The external preparation includes, selected among gallic acid derivatives of the following formula (I), 90% (% by weight herein and whenever it appears hereinafter) or over of one or more gallic acid derivatives (A) of the formula (I) wherein two of $R^2$, $R^3$, and $R^4$ independently represent a monosaccharide, disaccharide or oligosaccharide residue and from 0.001% to smaller than 10% of one or more gallic acid derivatives (B) of the formula (I) wherein one of $R^2$, $R^3$, and $R^4$ represents a monosaccharide, disaccharide or oligosaccharide residue, each based on the total content of the gallic acid derivatives of formula (I).

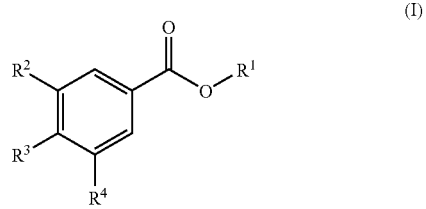

Note that $R^1$ represents a hydrogen atom, an alkali metal, an alkaline earth metal, an ammonium salt, or an alkyl or alkenyl group having from 1 to 18 carbon atoms, in which the alkali metal for $R^1$ includes Na, K, Li, or the like, the alkaline earth metal includes Ca, Mg, Ba, or the like, and the alkyl or alkenyl group should preferably have from 1 to 10 carbon atoms. $R^2$, $R^3$, and $R^4$ independently represent a hydrogen atom, a hydroxyl group, an alkoxy group having from 1 to 18 carbon atoms, preferably from 1 to 10 carbon atoms, a polyoxyethylene group, a polyoxypropylene group, or a monosaccharide, disaccharide, or oligosaccharide residue. The polyoxyethylene group is preferably of the formula, $-(OC_2H_4)_mH$ wherein m=1 to 100, preferably 2 to 40, and the polyoxypropylene group is preferably of the formula, $-(OC_3H_6)_nH$ wherein n=1 to 100, preferably 2 to 40. Specific examples of the monosaccharide, disaccharide or oligosaccharide residue include those residues of saccharides such as glucose, fructose, galactose, mannose, xylose, sucrose, lactose, stachyose, raffinose, fructooligosaccharide, galactooligosaccharide, lactosucrose, isomaltooligosaccharide, soybean oligosaccharide, xylobiose, and the like.

In the practice of the invention, one or more compounds (component A) of the formula (I) wherein two of $R^2$, $R^3$, and $R^4$ independently represent a monosaccharide, disaccharide, or oligosaccharide residue should be present in an mount of 90% or over, preferably 95% or over, and one or more compounds (component B) of the formula (I) wherein one of $R^2$, $R^3$, and $R^4$ represents a monosaccharide, disaccharide, or oligosaccharide residue should be present in an amount of from 0.001% to less than 10%, preferably from 0.01% to 5% each based on the total content of the gallic acid derivatives of formula (1). When the component B is formulated in an amount of 0.001% or over, one is enabled to suppress the component A from being settled at low temperatures, and satisfactory results are not obtained when using the component B in smaller amounts. The component B is poorer in high temperature stability in the course of preparation than the component A, so that if it is formulated in amounts of 10% or over, the resultant preparation may undergo a color change at high temperatures.

For example, the component A includes: gallic acid-3,5-diglucoside; gallic acid-3,4-diglucoside; methyl gallate-3,5-diglucoside; ethyl gallate-3,5-diglucoside; propyl gallate-3,5-diglucoside; butyl gallate-3,5-diglucoside; gallic acid-3,5-dimannoside; sodium gallate-3,5-diglucoside; ammonium gallate-3,5-diglucoside. Preferably, gallic acid-3,5-glucoside is used.

On the other hand, the component B includes, for example, gallic acid-3-glucoside, methyl galate-3-glucoside, ethyl galate-3-glucoside, propyl galate-3-glucoside, gallic acid-4-glucoside, sodium gallic acid-3-glucoside, ammonium gallic acid-4-glucoside, gallic acid-3-mannoside, gallic acid-4-mannoside, methyl galate-4-mannoside and the like.

It will be noted that gallic acid derivatives of the formula (I) other than the components (A) and (B) may be contained in amounts of not larger than 5%, preferably not larger than 1% based on the total content of the gallic acid derivatives of formula (1).

So far as the gallic acid derivatives used in the invention consist of those compounds defined hereinabove, they may be ones that are extracted from plants or are obtained by synthesis, and may be ones that are either anhydrous or hydrous. Although the preparation of the gallic acid derivatives is not critical, the derivatives can be readily and efficiently prepared, for example, by reacting gallic acid or its ester with a saccharide whose hydroxyl groups are partially or fully acetylated or a saccharide halogenated at the anomer position thereof in a solvent in the presence of an acid catalyst such as, for example $BF_3/Et_2O$, $SnCl_4$, $ZnCl_2$, or the like to obtain a glucosylated product, followed by protective-group elimination reaction in the presence of an acid or an alkali, if necessary, and purification by extraction or column chromatography.

The total content of the gallic acid derivatives is not critical in the practice of the invention. When the preparation for external use is applied to as a hair cosmetic, the derivatives can be formulated at a concentration of 0.01 to 20%, preferably from 0.1 to 10%, based on the total amount of the external preparation. If the total content is smaller than 0.01%, the effect of the gallic acid derivatives may not be obtained satisfactorily. On the other hand, when the total content exceeds 20%, a further increasing effect is not expected, with the possibility of poor economy.

The external preparation according to the invention should preferably contain a cationic surface active agent. Examples of the cationic surface active agent include those indicated below.

(1) Amine Salts and Ammonium Salts

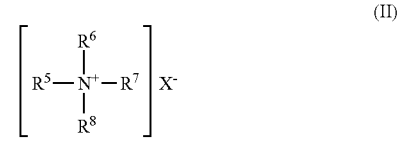

(II)

wherein $R^5$, $R^6$, $R^7$, and $R^8$ independently represent a hydrogen atom, an alkyl group, a hydroxyalkyl group, an alkenyl group, an polyalkylene oxide, or a benzyl group provided that one or two of $R^5$, $R^6$, $R^7$, and $R^8$ independently represent a linear or branched alkyl group, hydroxyalkyl group, or alkenyl group having from 8 to 24 carbon atoms, and the others may be the same or different and independently represent a hydrogen atom, a methyl group, an ethyl group, a benzyl group, or an polyalkylene oxide group, which is represented by $-(C_2H_4O)_qH$ or $-(C_3H_6O)_rH$ wherein q and r are an integer of 1 to 5 respectively; X represents an anion derived from an inorganic or organic acid such as a chloride, a bromide, a iodide, a sulfate, a methylsulfate, an ethylsulfate, an acetate, a pyrrolidonecarboxylate, a glycolate, a citrate, a succinate, a p-toluenesulfonate, a pyroglutaminate, a high fatty acid salt, an acidic amino acid salt, or the like.

(2) Guanidine Salts

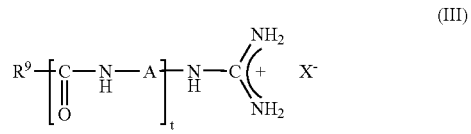

(III)

wherein $R^9$ represents a linear or branched alkyl group or alkenyl group having from 1 to 21 carbon atoms; A represents a linear or branched alkylene group or alkenylene group having from 1 to 10 carbon atoms; t is an integer of 1 to 5 provided that if t is 2 or over, A in the respective moieties may be the same or different; X has the same meaning as defined in the formula (II).

(3) Benzethonium Salts

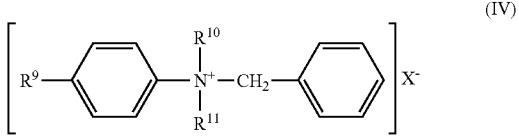

(IV)

wherein $R^9$ has the same meaning as defined above; $R^{10}$ and $R^{11}$ may be the same or different and independently represent a hydrogen atom, a methyl group, an ethyl group, a benzyl group, or an polyalkylene oxide group, which is represented by, $-(C_2H_4O)_qH$ or $-(C_3H_6O)_rH$ wherein q and r are an integer of 1 to 5 respectively; X has the same meaning as defined above.

(4) Pyridinium Salts

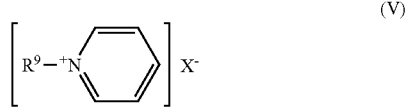

(V)

wherein $R^9$ and X respectively have the same meanings as defined above.

(5) Pyrrolidonecarboxylates

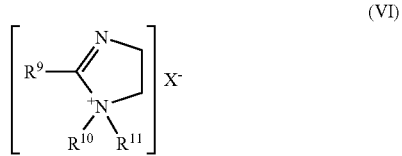

(VI)

wherein $R^9$, $R^1$, $R^{11}$, and X respectively have the same meanings as defined above.

Mention is also made of other types of amino acid-based cationic surface active agents such as lower alkyl esters of mono-N-long chain acyl group-bearing basic amino acids. The basic amino acids of the compounds include, for example, natural amino acids such as ornithine, lysine, arginine, and the like. Alternatively, synthetic amino acids such as α,γ-diaminobutyric acid may also be used. These may be either an optical active substance or a racemic substance. The acyl group includes a saturated or unsaturated higher fatty acid residue having from 8 to 22 carbon atoms. These may be either of a natural origin or of a synthetic type. For instance, single higher fatty acid residues such as a lauroyl group, a myristoyl group, a palmitoyl group, a stearoyl group, and the like may be adapted. In addition, natural mixed higher fatty acid residues such as coconut oil fatty acid residues and tallow high fatty acid residues may be adopted. The lower alkyl ester components preferably include a methyl ester, an ethyl ester, a propyl ester, a butyl ester, a pentyl ester, a hexyl ester, a heptyl ester, and an octyl ester. The counter ion includes ones as defined with respect to X in the foregoing formulas.

Specific examples of the cationic surface active agent include stearyltrimethylammonium chloride, cetyltrimethyl- ammonium chloride, behenyltrimethylammonium chloride, distearyldimethylammonium chloride, dioleyldimethylammonium chloride, didecyldimethylammonium chloride, lauric acid amide butylguanidine acetate, myristic acid amide butylguanidine acetate, palmitic acid amide butylguanidine acetate, distearyldimethylammonium sulfate, stearylethyldihydroxyethylammonium sulfate, N-coconut oil fatty acid L-arginine ethyl/DL-pyrrolidone carboxylate, and the like. These may be used singly or in combination of two or more. Of these, stearyltrimethylammonium chloride, distearyldimethylammonium chloride, and lauric acid amide butylguanidine acetate are preferred.

In the external preparation of the invention, the content of the cationic surface active agent can be appropriately controlled depending on the purpose in end use of the preparation and is not critical. Where the external preparation is employed as a hair cosmetic, the content ranges from 0.01 to 20%, preferably from 0.1 to 15% and more preferably from 0.1 to 10% based on the total amount of the external preparation. If the content is smaller than 0.01%, the low temperature stabilizing effect of a cationic surface active agent cannot be obtained satisfactorily. In contrast, when the content exceeds 20%, a further effect may not be expected, which may result in poor economy.

Water used in the invention is not critical in type, and city water, ion-exchanged water, distilled water, natural water, or the like may be used. A polar organic solvent is also not critical, and those ordinarily employed for preparations for external use are used, of which ethanol or isopropanol is preferred.

The preparation for external use according to the invention should be preferably formulated further with a silicone compound so as to improve the usability upon application to hair. Examples of the silicon compound include dimethylpolysiloxanes (including highly polymerized dimethylpolysiloxane and silicone rubbers), methylphenyl-polysiloxane, polyether-modified silicones, amino-modified silicones, betaine-modified silicones, alcohol-modified silicone, fluorine-modified silicones, epoxy-modified silicones, mercapto-modified silicones, carboxy-modified silicones, fatty acid-modified silicones, silicone-grafted polymers, cyclic silicones, alkyl-modified silicones, trimethylsilyl-terminated dimethylpolysiloxane, silanol group-terminated dimethylpolysiloxane, crosslinking alkyl polyether-modified silicones, and the like. Of these, polyether-modified silicones and amino-modified silicones are preferably used. These silicone compounds may be used as an emulsion by preparation with use of a surface active agent.

Although the viscosity of the silicones (except for the emulsion type) is not critical, the viscosity at 25° C. is preferably in the range of 10 to 1,000,000 $mm^2/S$, more preferably 30 to 100,000 $mm^2/s$, when taking the usability as a hair cosmetic into account.

In this connection, the amount of a silicone compound is appropriately selected and is usually in the range of 0.01 to 20%, preferably from 0.1 to 10%, based on the total of the preparation for external use.

Moreover, for the purpose of imparting stiffness and elasticity to hair, it is preferred to formulate 0.0001 to 1% of gallic acid and/or 0.0001 to 5% of sodium sulfate. Gallic acid may be one extracted from a natural product or obtained by synthesis, or may be anhydrous or hydrous. Sodium sulfate may be either anhydrous or hydrous.

Where an external preparation including a gallic acid glucoside, a cationic surface active agent, and a silicone compound as set forth hereinabove is applied as a hair cosmetic, a raspiness of hair, particularly a raspiness of hair damaged by chemical treatments such as of a permanent or hair coloring, daily exposure to UV light, or by blowing with a dryer, can be improved.

Hitherto, improvements in raspiness of hair have been frequently limited to the raspiness in a wet condition experienced mainly after shampooing. Most of the improvements are made by formulating cationized compounds in shampoos or the like (Japanese Patent Laid-open Nos. Hei 04-273811, Hei 06-40864, Hei 06-345620, Hei 08-143432, etc.) and by formulating silicones (Japanese Patent Laid-open Nos. Hei 06-32724, Hei 07-285836, Hei 07-316024, Hei 08-310922, Hei 09-124437, etc.), and limiting the types of activator species for detergents (Japanese Patent Laid-open Nos. Hei 05-124921, Hei 05-125392, Hei 06-40864, Hei 07-258044, Hei 08-12993, Hei 08-143432, Hei 09-157140, etc.). However, limitation is placed on their use in bath in most cases, with the effect thereof being not satisfactory.

The present inventors found that a raspiness of hair can be remarkably improved by that combination of such gallic acid glucoside, cationic surface active agent, and silicon compound set out hereinabove are applied to hair.

When such a gallic acid glucoside is formulated with ethyl alcohol, a hair cosmetic is obtained. In this case, 0.01 to 10%, preferably 0.1 to 5%, and more preferably 0.1 to 2% of a gallic acid glucoside and 5 to 90%, preferably 10 to 60%, and more preferably 10 to 30% of ethyl alcohol are combined, if necessary, together with 0.01 to 10%, preferably 0.1 to 5%, and more preferably 0.1 to 3% of a surface active agent and/or 0.01 to 30%, preferably 0.1 to 10%, and more preferably 0.1 to 5% of a high molecular weight compound, thereby providing a hair cosmetic. When this cosmetic is applied to hair, the gallic acid glucoside is allowed to be fully infiltrated inside the hair, thereby obtaining a high color degradation preventing effect. When using the hair cosmetic, dyed hair can be prevented from color degradation and dulling with time. Therefore, the cosmetic is able to keep the hair color that is immediately after dyeing.

The preparation for external use according to the invention may further includes, aside from the essential components, various types of components ordinarily employed in cosmetics, quasi drugs, medicines, and the like within ranges of amounts not impeding the effect of the invention, if necessary. Such components include, for example, anionic surface active agents such as sodium α-olefinsulfonates, potassium α-olefinsulfonates, sodium stearate, sodium palmitate, sodium laurate, sodium coconut oil fatty acid salt, arginine stearate, arginine palmitate, arginine laurate, coconut oil fatty acid salt of arginine, sodium laurylsulfate, sodium polyoxyethylene alkyl ether sulfates, ammonium polyoxyethylene alkyl ether sulfates, sodium polyoxyethylene alkyl ether phosphates, sodium polyoxyethylene polyoxypropylene alkyl ether phosphates, sodium lauroyl sarcosine, sodium coconut oil fatty acid salt of methyl-β-alanine, sodium dioctylsulfosuccinate, disodium polyoxyethylene alkylsulfosuccinate, sodium polystyrenesulfonate, disodium sulfosuccinate, sodium N-lauroyl-N-methyl-β-alanine, sodium malic acid monolaurylamide, and the like; amphoteric surface active agents such as 2-alkyl-N-carboxyethyl-N-hydroxyethylimidazolinium betaine, coconut oil fatty acid amidopropyl betaine, lauric acid amidopropyl betaine, lauryldimethylaminoacetic acid betaine, hydrogenated soybean phospholipid, alkyldiaminoethylglycine hydrochloride, N-[3-alkyloxy-2-hydroxypropyl]-L-arginine hydrochloride, sodium laurylaminopropionate, and the like; nonionic surface active agents such as sugar fatty acid esters, sorbitan fatty acid esters, sorbitol fatty acid esters, polyglycerine fatty acid esters, glycerine fatty acid esters, polyoxyethylene alkyl ethers, polyoxyethylene phytosterol ether, polyoxyethylene polyoxypropylene alkyl ethers, polyoxyethylene polyoxypropylene phytosterol ethers, hydrogenated castor oil, hydrogenated castor oil fatty acid esters, polyoxyethylene hydrogenated castor oil, polyoxyethylene polyoxypropylene hydrogenated castor oil, polyoxyethylene hydrogenated castor oil fatty acid esters, polyoxyethylene polyoxypropylene hydrogenated castor oil fatty acids, and the like; oils such as isopropyl myristate, isopropyl palmitate, ethyl oleate, octyldodecyl neopentanoate, butyloctyl salicylate, cholesteryl stearate, polyoxyethylene, liquid paraffin, liquid isoparaffin, squalene, squalane, castor oil, jojoba oil, hazelnut oil, sweet almond oil, grape seed oil, sasanqua oil, safflower oil, olive oil, meadow home oil, rose hip oil, avocado oil, and like; polymers such as hydromethyl cellulose, hydroxyethyl cellulose, hydroxypropyl cellulose, cationized cellulose, polyvinyl pyrrolidone, polyvinyl alcohol, acrylic acid/methacrylic acid copolymer, carboxyvinyl polymer, and the like; amino acid such as glycine, ornithine, methionine, alanine, arginine, glutamine, cysteine, cysteic acid, cystine, leucine, isoleucine, aspartic acid, lysine, phenyl alanine, and the like; plant extracts such as of rosemary, capsicum, rumex japonicus, aloe, lycium chinese, mugwort, mustard, rice plant, licorice, Cape jasmine, white birch, sophorae radix, sponge cucumber, eucalyptus, arnica, and the like; extracts of algae such as kelp, chlorella, ascophyllum nodosum, coralline algae, eucheuma, and the like; polyhydric alcohols such as propylene glycol, dipropylene glycol, glycerine, butylene glycol, and the like; preservatives such as paraoxybenzoates, paraoxybenzoic esters, and the like; sequestering agents such as edetates, pyrophosphates, citrates, glycolates, tartaric acid, and the like; gases such as liquefied petroleum gas, dimethyl ether, nitrogen, carbon dioxide gas, and the like; antioxidants such as dibutylhydroxytoluene, butylhydroxyanisole, erythorbic acid, dilauryl thiopropionate, sodium sulfate, sodium sulfite, tocopherol, ascorbyl dipalmitate, and the like; UV absorbers such as p-aminobenzoic acid derivatives, salicylic acid derivatives, cinnamic acid derivatives, oxybenzone, dioxybenzone, dihydroxydimethoxybenzophenone, and the like; pH adjusting agents such as succinic acid, citric acid, tartaric acid, lactic acid, glycolic acid, and the like; vitamins, dyes, refrigerant such as 1-menthol and derivative of thereof, humectants, thickeners, and the like.

The perfume composition may be formulated in the preparation for external use of the invention. In this case, the perfume composition is preferably formulated in an amount of 0.00001 to 10%, more preferably 0.0001 to 5%, based on the total of the external composition.

The form of the external preparation is not critical and the preparation may be used, for example, in various forms of a solution, an emulsion, a dispersion, an oil-water double-layered system and can be used in the forms of an aerosol, a tick, a gel, a cream, a lotion, and the like. Further, the preparation for external use of the invention may be impregnated in a non-woven fabric for use as a sheet. Thus, the external preparation may be utilized as a hair tonic, a hair liquid, a hair lotion, a hair spray, a shampoo, a rinse, a conditioner, a treatment, a skin cream, a skin lotion, a whitening, a shaving gel, or the like. These may be prepared according to ordinary methods for individual forms. Where a container is used in practical applications, its material and shape are, respectively, not limited to specific ones. The materials for this include polypropylene, polyethylene terephthalate, polyethylene, EVAL (ethylene vinyl alcohol copolymer resin), and laminates thereof, laminates having an aluminum foil layer, tinplate, aluminum, glass, and the like. The types of containers include ordinarily employed ones such as a trigger-type container, a pump-type container, an aerosol container, a tubular container, a telescopic container, a roll-on container, a jar container, a pillow pack, a portion container, capsules, and the like.

The external preparation of the invention can be used in all of various types of external preparations (including preparations used for animals). More particularly, mention is made of medicines, quasi medicines, and cosmetics for local or general purposes (including, for example, a body soap, a skin cream, a whitening, a shampoo, a rinse, a conditioner, a treatment, a permanent liquid, a hair dye, a hair dressing, a hair tonic, a hair growth, remedy tonic, and the like), all in the form of capsules, a liquid, a gel, an ointment, tablets and granules. Especially, the preparation of the invention is preferred as a hair cosmetic.

EXAMPLE

The invention is described particularly by way of examples, which should not be construed as limiting the invention thereto. Comparative examples are also described. In these examples, percent is by weight.

Examples 1 to 16 and Comparative Examples 1 to 4

Samples of Examples 1 to 16 and Comparative Examples 1 to 4 having formulations indicated in Tables 1 and 2 were respectively prepared in a usual manner, and each was placed in a 50 ml glass container, followed by allowing to stand in an air-cooling/heating thermostatic chamber at −10° C. and 50° C. for evaluation by determination of the days before a precipitate was recognized through visual observation and the days before the preparation underwent a color change. The results are shown in Tables 1 and 2. It will be noted that the pH was adjusted to 3 to 7 by use of glucollic acid or glycolic acid.

Evaluation of stability: ×=0 to 14 days, Δ=15 to 30 days, ○=31 to 40 days, ◉=41 days or over

TABLE 1

Unit: %

| | Examples | | | | | | | | Comparative Examples | |
|---|---|---|---|---|---|---|---|---|---|---|
| Component | 1 | 2 | 3 | 4 | 5 | 6 | 7 | 8 | 1 | 2 |
| Gallic acid-3,5-diglucoside | 1.0 | 1.0 | 1.0 | | | | | | 1.0 | |
| Methyl gallate-3,5-diglucoside | | | | 1.0 | 1.0 | | | | | |
| Ethyl gallate-3,5-diglucoside | | | | | | 1.0 | | | | |
| Propyl gallate-3,5-diglucoside | | | | | | | 1.0 | | | |
| Gallic acid-3,5-dimaltoside | | | | | | | | 1.0 | | 1.0 |
| Gallic acid-3-glucoside | 0.05 | | 0.02 | 0.01 | | 0.01 | 0.01 | | | 0.2 |
| Methyl gallate-3-glucoside | | 0.05 | 0.02 | | 0.01 | 0.01 | | 0.01 | | |
| Stearyltrimethylammonium chloride | | | | 1.0 | 1.0 | 0.5 | 0.5 | 0.5 | | |
| Butylene-1,3-glycol | 5.0 | 5.0 | 5.0 | 5.0 | 5.0 | 5.0 | 5.0 | 5.0 | 5.0 | 5.0 |
| Aminoethylaminopropylmethylsiloxane/dimethylsiloxane copolymer emulsion | 1.0 | 1.0 | 1.0 | 1.0 | 1.0 | 1.0 | 1.0 | 1.0 | 1.0 | 1.0 |
| Glucollic acid | Appropriate amount | Appropriate amount | Appropriate amount | Appropriate amount | Appropriate amount | Appropriate amount | Appropriate amount | Appropriate amount | Appropriate amount | Appropriate amount |
| Disodium edetate | 0.1 | 0.1 | 0.1 | 0.1 | 0.1 | 0.1 | 0.1 | 0.1 | 0.1 | 0.1 |
| Ethanol | 20 | 20 | 20 | 20 | 20 | 20 | 20 | 20 | 20 | 20 |
| Water | Balance | Balance | Balance | Balance | Balance | Balance | Balance | Balance | Balance | Balance |
| Total (%) | 100.0 | 100.0 | 100.0 | 100.0 | 100.0 | 100.0 | 100.0 | 100.0 | 100.0 | 100.0 |
| Low temperature stability | ○ | ○ | ◉ | ○ | ○ | ◉ | ○ | ○ | X | ○ |

TABLE 1-continued

|  | Examples | | | | | | | | Comparative Examples | |
|---|---|---|---|---|---|---|---|---|---|---|
| Component | 1 | 2 | 3 | 4 | 5 | 6 | 7 | 8 | 1 | 2 |
| High temperature stability | ⊚ | ⊚ | ⊚ | ⊚ | ⊚ | ⊚ | ⊚ | ⊚ | ⊚ | X |

Unit: %

TABLE 2

|  | Examples | | | | | | | | Comparative Examples | |
|---|---|---|---|---|---|---|---|---|---|---|
| Component | 9 | 10 | 11 | 12 | 13 | 14 | 15 | 16 | 3 | 4 |
| Gallic acid-3,5-diglucoside | 2.0 | | | | 1.0 | | 1.0 | | 1.0 | |
| Gallic acid-3,5-dimaltoside | | 2.0 | | | 1.0 | | 1.0 | | 1.0 | |
| Ethyl gallate-3,5-dimaltoside | | | 2.0 | | | 1.0 | | 1.0 | | 1.0 |
| Propyl gallate-3,5-dimaltoside | | | | 2.0 | | 1.0 | | 1.0 | | 1.0 |
| Gallic acid-3,5-glucoside | 0.1 | | | | | | | | | |
| Ethyl gallate-3-glucoside | | 0.1 | | | | | | | | |
| Propyl gallate-3-glucoside | | | 0.1 | | | | | | | |
| Methyl gallate-3-maltoside | | | | 0.1 | | | | | | |
| Ethyl gallate-3-maltoside | | | | | 0.1 | | 0.1 | | | |
| Propyl gallate-3-maltoside | | | | | | 0.1 | | 0.1 | | |
| Stearyltrimethyl-ammonium chloride | 0.5 | 0.5 | 0.5 | 0.5 | 0.5 | 0.5 | | | | 0.5 |
| Gallic acid | 0.001 | 0.001 | 0.001 | 0.001 | 0.001 | 0.001 | 0.001 | 0.001 | 0.001 | 0.001 |
| Sodium sulfate | 0.001 | 0.001 | 0.001 | 0.001 | 0.001 | 0.001 | 0.001 | 0.001 | 0.001 | 0.001 |
| Aminoethylamino-propylmethyl-siloxane/dimethyl-siloxane copolymer emulsion | 1.0 | 1.0 | 1.0 | 1.0 | 1.0 | 1.0 | 1.0 | 1.0 | 1.0 | 1.0 |
| Lauryldimethylamino acetic acid betaine | 3.0 | 3.0 | 3.0 | 3.0 | 3.0 | 3.0 | 3.0 | 3.0 | 3.0 | 3.0 |
| propylene glycol | 5.0 | 5.0 | 5.0 | 5.0 | 5.0 | 5.0 | 5.0 | 5.0 | 5.0 | 5.0 |
| glycolic acid | Appropriate amount | Appropriate amount | Appropriate amount | Appropriate amount | Appropriate amount | Appropriate amount | Appropriate amount | Appropriate amount | Appropriate amount | Appropriate amount |
| sodium pyrophosphate | 0.1 | 0.1 | 0.1 | 0.1 | 0.1 | 0.1 | 0.1 | 0.1 | 0.1 | 0.1 |
| Hydroxyethylcellulose | 2.0 | 2.0 | 2.0 | 2.0 | 2.0 | 2.0 | 2.0 | 2.0 | 2.0 | 2.0 |
| Ethanol | 15 | 15 | 15 | 15 | 15 | 15 | 15 | 15 | 15 | 15 |
| Water | Balance | Balance | Balance | Balance | Balance | Balance | Balance | Balance | Balance | Balance |
| Total (%) | 100.0 | 100.0 | 100.0 | 100.0 | 100.0 | 100.0 | 100.0 | 100.0 | 100.0 | 100.0 |
| Low temperature stability | ⊚ | ○ | ○ | ⊚ | ⊚ | ⊚ | ○ | ○ | X | Δ |
| High temperature stability | ⊚ | ○ | ⊚ | ⊚ | ⊚ | ○ | ⊚ | ○ | ⊚ | ⊚ |

Unit: %

Examples 17, 18, and Comparative Examples 5 to 8

Out-bath hair care products having the formulations indicated in Table 3 were prepared and subjected to evaluation of a raspiness of hair in the following way.

Evaluation Method

Twenty panelists who had suffered hair damages through hair coloring or a permanent were each applied with each of the hair care products to evaluate a raspiness of hair after the application in comparison with that prior to the application on the basis of the following evaluation standards.

<Evaluation standards>

⊙: Panelists who answered as better after the application than before is not smaller than 16 in number among 20.

○: Panelists who answered as better after the application than before is 10 to 15 in number among 20.

Δ: Panelists who answered as better after the application than before is 4 to 9 in number among 20.

x: Panelists who answered as better after the application than before is smaller than 4 in number among 20.

TABLE 3

| Formulation component | Examples | | Comparative Examples | | | |
|---|---|---|---|---|---|---|
| (%) | 17 | 18 | 5 | 6 | 7 | 8 |
| Gallic aid-3,5-diglucoside | 1 | 0.5 | | 1 | 1 | |
| Gallic aicd-3-glucoside | 0.05 | 0.02 | | | | |
| Stearyltrimethyl-ammonium chloride note 1 | 1 | 1 | 1 | | 1 | |
| Silicone 1 note 2 | 5 | | 5 | 5 | | |
| Silicone 2 note 3 | | 10 | | | | |
| Polyoxyethylene (30) stearyl ether note 4 | 0.2 | 0.2 | 0.2 | 0.2 | 0.2 | 0.2 |
| Liquid paraffin | | 10 | | | | |
| Ethanol | 10 | 10 | 10 | 10 | 10 | 10 |
| Perfume | 0.1 | 0.1 | 0.1 | 0.1 | 0.1 | 0.1 |
| Purified water | Balance | Balance | Balance | Balance | Balance | Balance |
| Total | 100 | 100 | 100 | 100 | 100 | 100 |
| Raspiness | ⊚ | ⊚ | Δ | Δ | ○ | X |

Note 1: ARQUAD T-800 (Lion Chemical Co., Ltd.)
Note 2: KSG 21 (Shin-Etsu Silicone Co., Ltd.; crosslinked type polyether-modified silicone/methylpolysiloxane mixture)
Note 3: KSG 31 (Shin-Etsu Silicone Co., Ltd.; crosslinked type alkyl polyether-modified silicone/liquid paraffin mixture)
Note 4: EMALEX 630 (Nippon Emulsion Co., Ltd.)

Example 19

A Water Preparation

A dispenser-type water preparation having the following formulas was prepared and filled in a UV absorber-built-in PET pump dispenser container.

| | |
|---|---|
| Gallic aicd-3,5-diglucoside | 0.4% |
| Gallic aicd-3-glucoside | 0.01 |
| Sodium sulfate | 0.001 |
| Lauryldimethylaminoacetic acid betaine | 5.0 |
| Stearyltrimethylammonium chloride | 3.0 |
| N-Vinylpyrrolidone-N,N-dimethylaminoethyl methacrylate | 0.5 |
| N-Methacryloyloxydiethyl-N,N-dimethylaminoethyl-α-N-methylcarboxy betaine/alkyl ester methacrylate copolymer (Yukafoamer 510, made by Mitsubishi Chemical Corporation) | 1.0 |
| Hydrolyzed keratin (Proticute U-alpha, made by ICHIMARU PHARCOS Co., Ltd.) | 2.5 |
| Hydroxybenzophenone | 0.1 |
| Methylparaben | 0.1 |
| Propylparaben | 0.1 |
| Sodium anhydrous pyrophosphate | 0.05 |
| Glycolic acid | 0.2 |
| Triethanolamine | 1.0 |
| Perfume | 0.1 |
| Ethanol | 20.0 |
| Purified water | balance |
| Total | 100.0% |

Example 20

Aerosol Hair Tonic

A hair tonic having the following formula was prepared and filled in an aluminum aerosol pressure can.

(Stock Solution)

| | |
|---|---|
| Methyl gallate-3,5-diglucoside | 0.25% |
| Gallic acid-3-glucoside | 0.02 |
| Sodium sulfate | 0.005 |
| Coconut oil fatty acid amidopropyl-dimethylaminoacetic acid betaine | 1.0 |
| Distearyldimethylammonium chloride | 1.5 |
| dl-α-tocopherol acetate | 0.5 |
| 1-Menthol | 0.2 |
| Perfume | 0.05 |
| Ethanol | 40.0 |
| Purified water | balance |
| Total (Gases) | 60.0 |
| LPG | 30.0 |
| Dimethyl ether | 10.0 |
| Total | 100.0% |

Example 21

Non-Aerosol Pump Foam Preparation

A foam preparation having the following formulation was prepared and filled in a pump foam container made of UV absorber-built-in polypropylene. It will be noted that the pH was adjusted to 4.5.

| | |
|---|---|
| Gallic aicd-3,5-dimaltoside | 0.2% |
| Gallic aicd-3-glucoside | 0.015 |
| Sucrose ester laurate | 0.5 |
| Butylguanidine-acetic acid lauric acid amide | 1.0 |
| 3-Methyl-1,3-butandiol | 10.0 |
| Silicone emulsion (FZ-4188, made by Nippon Unicar Co., Ltd.) | 8.0 |
| Amino-modified silicone emulsion (FZ-4672, made by Nippon Unicar Co., Ltd.) | 5.0 |
| Polyoxy ethylene (30) stearyl ether | 0.6 |
| Luaryldimethylamine oxide | 0.5 |
| Plant-derived squalane | 0.1 |

-continued

| | |
|---|---|
| Water-soluble collagen (Neptigen, atelo type, made by ICHIMARU PHARCOS Co., Ltd.) | 1.0 |
| Methylparaben | 0.1 |
| Propylparaben | 0.05 |
| Benzalkonium chloride | 0.1 |
| Dihydroxybenzophenonesulfonic acid (trihydrate) | 0.1 |
| Citric acid | 0.5 |
| Triethanolamine | appropriate amount |
| Perfume | 0.1 |
| Ethanol | 20.0 |
| Purified water | balance |
| Total | 100.0% |

Example 22

Trigger-Type Hair Treatment

A hair treatment having the following formulation was prepared and filled in a PET container of a trigger type. The pH was adjusted to 4.3.

| | |
|---|---|
| Gallic aicd-3,5-diglucoside | 0.3% |
| Gallic aicd-3-glucoside | 0.012 |
| Gallic acid | 0.001 |
| Sodium sulfate | 0.001 |
| Lauryldimethylaminoacetic acid betaine | 1.5 |
| Stearyltrimethylammonium chloride | 2.0 |
| Polyoxypropylene (9) diglyceryl ether | 1.0 |
| Propylene glycol | 4.0 |
| Polyoxyethylene/methylpolysiloxane copolymer | 1.0 |
| Hydrolyzed silk solution (Silkgen G Soluble S, made by ICHIMARU PHARCOS Co., Ltd.) | 1.0 |
| Hydroxypropylchitosan liquid (Chitofilmer, made by ICHIMARU PHARCOS Co., Ltd.) | 1.0 |
| Dihydroxybenzophenonesulfonic acid | 0.1 |
| Methylparaben | 0.1 |
| Anhydrous sodium pyrophosphate | 0.05 |
| Citric acid | appropriate amount |
| Sodium citrate | appropriate amount |
| Ethanol | 20.0 |
| Perfume | 0.05 |
| Purified water | balance |
| Total | 100.0% |

Example 23

Gel

A gel having the following formulation was prepared and filled in a pump-type container made of UV absorber-built-in PET. The pH was adjusted to 4.4 with a viscosity being adjusted to 1500 to 3000 Pa·s.

| | |
|---|---|
| Ellagic acid | 0.05% |
| Gallic aicd-3,5-diglucoside | 0.5 |
| Gallic aicd-3-glucoside | 0.001 |
| Gallic acid | 0.0005 |
| Sodium sulfate | 0.001 |
| Stearyltrimethylammonium chloride | 2.5 |
| Polyoxyethylene (40) hydrogenated castor oil | 3.0 |
| Silicone emulsion (FZ-4188, made by Nippon Unicar Co., Ltd.) | 5.0 |
| Polyoxyethylene/methylpolysiloxane copolymer | 1.0 |
| Chamomile extract | 1.0 |

-continued

| | |
|---|---|
| Leaf extract of Japanese medlar | 1.0 |
| Decaglyceryl monoisostearate | 2.0 |
| Dihydroxybenzophenone | 0.1 |
| Hydroxyethyl cellulose | appropriate amount |
| Methylparaben | 0.3 |
| Anhydrous sodium pyrophosphate | 0.2 |
| Sodium sulfite | 0.1 |
| Glycolic acid | appropriate amount |
| Dibutylhydroxytoluene | 0.001 |
| Ethanol | 20.0 |
| Perfume | 0.05 |
| Purified water | balance |
| Total | 100.0% |

Example 24

Pump Dispenser Hair Mist

A hair mist having the following formulation was prepared and filled in a pump dispenser container made of polyethylene. The pH was adjusted to 5.0.

| | |
|---|---|
| Gallic aicd-3,5-diglucoside | 0.5% |
| Gallic aicd-4-glucoside | 0.005 |
| Sodium sulfate | 0.001 |
| N-coconut oil fatty acid L-arginine ethyl/DL-Pyrrolidonecarboxylate | 2.0 |
| Wax emulsion* | 5.0 |
| 70% sorbitol solution | 1.0 |
| White birch extract | 1.0 |
| Polyoxyethylene/methyl polysiloxane copolymer | 0.5 |
| Blue berry extract | 0.5 |
| Oxybenzone | 0.1 |
| Methylparaben | 0.3 |
| Citric acid | appropriate amount |
| Sodium citrate | appropriate amount |
| Perfume | 0.2 |
| Ethanol | 15.0 |
| Purified water | balance |
| Total | 100.0 |

*Emulsification of 5% of carnauba wax, 7% of polyoxyethylene (15) lauryl ether and 88% of purified water by 90° C. (with an average particle size of 100 nm).

Example 25

Aerosol Foam

An aerosol foam having the following formulation was prepared. A container used was an aluminum pressure can.

| | |
|---|---|
| (Stock solution) | |
| Gallic acid-3,5-diglucoside | 1.0% |
| Gallic acid-4-glucoside | 0.01 |
| Sodium sulfate | 0.005 |
| Cationized cellulose (XK-503, made by Lion Corporation) | 0.4 |
| Sodium hyaluronate | 1.0 |
| Dipropylene glycol | 6.0 |
| Stearyltrimethylammonium chloride | 2.5 |
| Amino-modified silicone (SF8452C, made by Toray-Dow Corning Silicone Co., Ltd.) | 2.0 |
| Polyoxyethylene (60) hydrogenated castor oil | 1.0 |
| Hydrolyzed keratin | 1.0 |

| | |
|---|---|
| N-coconut oil fatty acid acyl-L-alginine ethyl/DL-pyrrolidonecarboxylate Trimethylglycine (Aquadew AN-100, made by Ajinomoto Co., Inc.) | 0.5 |
| | 0.5 |
| Carboxyvinyl polymer | 0.5 |
| Triethanolamine solution (30% aqueous solution) | 0.05 |
| Shea butter | 1.0 |
| Perfume | 0.1 |
| Ethanol | 20.0 |
| Purified water | balance |
| Total | 92.0 |
| (Gas) | |
| LPG gas | 8.0 |
| Total | 100.0% |

Example 26

Hair Wax

A hair wax having the following formulation was prepared and filled in a jar-type container made of antistatic agent and UV absorber-built-in polypropylene.

| | |
|---|---|
| Gallic acid-3,5-diglucoside | 0.5% |
| Gallic acid-3-glucoside | 0.01 |
| Dimyristyldimethylammonium chloride | 3.0 |
| Gallic acid | 0.001 |
| Sodium sulfate | 0.001 |
| Decaglyceryl diisostearate | 5.0 |
| Carboxyvinyl polymer | 0.5 |
| Xanthan gum | 0.25 |
| Water soluble solid silicone (KF-6004, made by Shin-Etsu Chemical Co. Ltd.) | 2.0 |
| Silicone powder (Tospearl 2000B, made by Toshiba Silicone Co., Ltd.) | 1.0 |
| Hydrolyzed silk solution (Silkgen G Soluble S, made by ICHIMARU PHARCOS Co., Ltd.) | 0.5 |
| Vaseline | 3.0 |
| Squalane | 2.0 |
| Candelilla wax | 1.0 |
| Apple extract | 2.0 |
| Polyoxypropylene (14) diglyceryl ether | 4.0 |
| Dihydroxybenzophenone | 0.1 |
| Methylparaben | 0.3 |
| Tetrasodium edetate | 0.05 |
| Triethanolamine | 0.5 |
| Perfume | 0.05 |
| Ethanol | 5.0 |
| Purified water | balance |
| Total | 100.0% |

Example 27

Gel

A gel having the following formulation was prepared and filled in a tube container made of antistatic agent and UV absorber-built-in polypropylene.

| | |
|---|---|
| Gallic acid-3,5-diglucoside | 0.5% |
| Gallic acid-4-mannosid | 0.02 |
| Stearyltrimethylammonium chloride | 5.0 |
| Sodium sulfate | 0.001 |
| Alkyl-modified carboxyvinyl polymer | 0.5 |

| | |
|---|---|
| Xanthan gum | 0.25 |
| Silicone paste (KSG-21, made by Sin-Etsu Chemical Co., Ltd.) | 5.0 |
| Water-soluble solid silicone (KF-6004, made by Sin-Etsu Chemical Co., Ltd.) | 2.0 |
| Silicone powder (Tospearl 2000B, made by Toshiba Silicone Co., Ltd.) | 1.0 |
| Hydrolyzed silk solution | 0.5 |
| Polyoxyethylene (20) stearyl ether | 4.0 |
| Hydroxybenzophenone | 0.1 |
| Methylparaben | 0.3 |
| Triethanolamine | 0.5 |
| Perfume | 0.05 |
| Ethanol | 15.0 |
| Purified water | balance |
| Total | 100.0% |

Example 28

Shampoo

A shampoo having the following formulation was prepared and filled in a pump container made of antistatic agent and UV absorber-built-in polypropylene.

| | |
|---|---|
| Gallic acid-3,5-diglucoside | 0.5% |
| Propyl gallate-3-mannoside | 0.01 |
| Behenyltrimethylammonium chloride | 0.5 |
| Sodium sulfate | 0.001 |
| Sodium lauryl ether sulfate | 10.0 |
| Sodium α-olefinsulfonate | 5.0 |
| Fatty acid diethanolamide | 5.0 |
| Alkylamidopropyl betaine | 5.0 |
| Highly polymerized dimethylsilicone (BY11-003, made by Toray-Dow Corning Silicone Co., Ltd.) | 3.0 |
| Cationized cellulose (XK-503, made by Lion Corp.) | 0.5 |
| Ethylene glycol distearate | 2.0 |
| Aroe extract | 0.2 |
| Sodium benzoate | 0.8 |
| Perfume | 0.05 |
| Purified water | balance |
| Total | 100.0% |

Example 29

Rinse

A rinse having the following formulation was prepared and filled in a pump container made of antistatic agent and UV absorber-built-in polypropylene.

| | |
|---|---|
| Gallic acid-3,5-diglucoside | 0.5% |
| Gallic acid-3-glucoside | 0.02 |
| Gallic acid | 0.002 |
| Sodium sulfate | 0.001 |
| Stearyltrimethylammonium chloride | 1.0 |
| Distearyldimethylammonium chloride | 0.5 |
| Cetostearyl alcohol | 3.0 |
| POE (5) stearyl ether | 1.5 |
| Liquid paraffin | 1.0 |
| Cyclomethicone (DC246, made by Toray-Dow Corning Silicone Co., Ltd.) | 0.5 |
| Dimethylsilicone (SH200-500cs, made by Toray-Dow Corning Silicone Co., Ltd.) | 5.0 |
| Mallow extract | 0.2 |
| Methyl paraben | 0.1 |

-continued

| | |
|---|---|
| Perfume | 0.1 |
| Purified water | balance |
| Total | 100.0% |

Example 30

Cream

A cream having the following formulations A and B was prepared by dissolving A and B at 70° C. respectively, adding A to B to obtain a uniform emulsion, followed by further adding C while cooling and filling in an aluminum-laminated tube.

| | |
|---|---|
| A Oil phase portion | |
| Squalane | 5.0% |
| Ethyl oleate | 2.0 |
| Octyldodecyl myristate | 1.5 |
| Liquid paraffin | 1.0 |
| Polyethylene glycol (40EO) monostearate | 3.0 |
| Coconut oil fatty acid sorbitan ester | 2.0 |
| Glycerine monostearate | 1.0 |
| Cetostearyl alcohol | 1.0 |
| Propylparaben | 0.1 |
| B Aqueous phase portion | |
| Gallic acid-3,5-dimaltoside | 0.5 |
| Gallic acid-4-maltoside | 0.03 |
| Palmityltrimethylammonium chloride | 0.3 |
| Sodium sulfate | 0.001 |
| Butylene-1,3-glycol | 2.5 |
| Dipropylene glycol | 2.5 |
| Methylparaben | 0.25 |
| Dipotassium glycyrrhizinate | 0.2 |
| Gentian extract | 0.1 |
| Purified water | balance |
| C Perfume | 0.05 |
| Total | 100.0% |

Example 31

Hair Tonic

A hair tonic having the following formulation was prepared and filled in a telescopic glass container.

| | |
|---|---|
| Ethyl gallate-3,5-diglucoside | 1.0% |
| Methyl gallate-3-glucoside | 0.05 |
| Pentadecanoyltriethylammonium chloride | 1.0 |
| Sodium sulfate | 0.007 |
| POE (8) oleyl alcohol ether | 1.5 |
| Glycerine | 3.0 |
| L-Menthol | 0.1 |
| Hinokitiol | 0.3 |
| Methylparaben | 0.1 |
| Perfume | 0.05 |
| Ethanol | 70.0 |
| Purified water | balance |
| Total | 100.0% |

Example 32

Hair Remedy and Growth Tonic

A hair remedy and growth tonic having the following formulation was prepared and filled in a telescopic polyethylene container.

| | |
|---|---|
| Ethyl gallate-3,5-diglucoside | 1.0% |
| Gallic acid-3-glucoside | 0.02 |
| Stearyltrimethylammonium chloride | 0.5 |
| POE (10) oleyl ether | 2.0 |
| DL-α-tocopherol acetate | 0.1 |
| Sucrose ester myristate | 0.5 |
| Biotin | 0.002 |
| Succinic acid | 0.3 |
| Swertia herb extract | 1.0 |
| Hinokitiol | 0.1 |
| L-Menthol | 0.3 |
| Methylparaben | 0.1 |
| Perfume | 0.05 |
| Ethanol | 40.0 |
| Purified water | balance |
| Total | 100.0% |

Example 33

Hair Growth Spray Tonic

A hair growth spray tonic having the following formulation was prepared and filled in a tin pressure can.

| | |
|---|---|
| (Stock solution) | |
| Methyl gallate-3,5-diglucoside | 0.3% |
| Methyl gallate-3-glucoside | 0.01 |
| Butylguanidine acetate stearate | 3.0 |
| N-Pentadecanoyl isoleucine | 0.3 |
| Sorbitan laurate | 1.0 |
| Amphoteric polymer (Yukafoamer 201, made by Mitsubishi Chemical Co., Ltd.) | 0.5 |
| Citric acid | 0.1 |
| Sucrose ester laurate | 2.5 |
| L-Menthol | 0.5 |
| Ethanol | 20.0 |
| Purified water | balance |
| Total | 80.0 |
| (Gas) | |
| LPG | 20.0 |
| Total | 100.0% |

Example 34

Aerosol Foam

An aerosol foam having the following formulation was sprayed and filled in a PET pressure can.

| | |
|---|---|
| Methyl gallate-3,5-diglucoside | 2.0% |
| Methyl gallate-3-glucoside | 0.005 |
| Sodium sulfate | 0.01 |
| EO-modified silicone | 4.0 |
| Piroctone olamin | 0.5 |
| Ethyl oleate | 3.0 |

-continued

| | |
|---|---|
| Amphoteric polymer (Yukafoamer 204, made by Mitsubishi Chemical Co., Ltd.) | 1.0 |
| Stearyltrimethylammonium chloride | 0.5 |
| POP (9) diglyceryl ether | 1.5 |
| POE (20) sorbitan monooleate | 0.5 |
| Perfume | 0.2 |
| Ethanol | 20.0 |
| Purified water | balance |
| Total | 80.0 |
| (Gas) | |
| LPG | 10.0 |
| DME | 10.0 |
| Total | 100.0% |

Example 35

Preparation for Fixing Mussy or Frizzy Hair

A preparation for fixing mussy or frizzy hair having the following formulation was prepared and filled in a PET container. The pH was adjusted to 6.

| | |
|---|---|
| Propyl gallate-3,5-diglucoside | 2.0% |
| Propyl gallate-3-glucoside | 0.01 |
| Sodium sulfate | 0.006 |
| Amino-modified silicone | 3.0 |
| Polyvinylpyrrolidone | 0.4 |
| Cationized cellulose (XK-503, made by Lion Corporation) | 0.5 |
| POP (14) diglyceryl ether | 4.0 |
| Arginine | 0.5 |
| Sorbitol solution | 2.5 |
| Stearyltrimethylammonium chloride | 0.5 |
| POE (50) hydrogenated castor oil | 0.5 |
| Oxybenzonesulfonic acid | 0.1 |
| Methylparaben | 0.1 |
| Dibutylhydroxytoluene | 0.05 |
| Perfume | 0.5 |
| Green No. 3 | very small amount |
| Citric acid | appropriate amount |
| Ethanol | 15.0 |
| Purified water | balance |
| Total | 100.0% |

Example 36

Gel for Eyebrow or Eyelashes

A gel for eyebrow or eyelashes having the following formulation was prepared and filled in a glass mascara container. The pH was adjusted to 7.

| | |
|---|---|
| Methyl gallate-3,5-dimaltoside | 2.0% |
| Methyl gallate-3-maltoside | 0.02 |
| Stearyltrimethylammonium chloride | 2.0 |
| Gallic acid | 0.002 |
| Sodium sulfate | 0.005 |
| Polyether-modified silicone (BY22-008M, made by Toray-Dow Corning Silicone Co., Ltd.) | 1.0 |
| Amphoteric polymer (Yukafoamer 205, made by Mitsubishi Chemical Co., Ltd.) | 1.0 |
| Carboxyvinyl polymer | 0.5 |
| Decaglycerine monoisostearate | 4.0 |
| POE (30) isocetyl ether | 0.5 |

-continued

| | |
|---|---|
| Methylparaben | 0.1 |
| Sodium hydrogensulfite | 0.05 |
| Disodium edetate | 0.05 |
| Perfume | 0.5 |
| Triethanolamine | appropriate amount |
| Ethanol | 10.0 |
| Purified water | balance |
| Total | 100.0% |

Example 37

Cream

The following formulations A, B were dissolved at 70° C. respectively, and B was added to A to make a uniform emulsion, followed by further addition of C while cooling to prepare a cream. This was filled in a polyethylene tubular container.

| | |
|---|---|
| A Oil phase portion | |
| Liquid paraffin | 5.0% |
| Squalane | 15.0 |
| Cetostearyl alcohol | 5.0 |
| Glycerine monostearate | 2.0 |
| POE (20) sorbitan monolaurate | 2.0 |
| Propylparaben | 0.1 |
| B Aqueous phase portion | |
| Methyl gallate-3,5-dimaltoside | 2.0 |
| Methyl gallate-3-maltoside | 0.1 |
| Distearyldimethylammonium chloride | 0.1 |
| Gallic acid | 0.001 |
| Sodium sulfate | 0.001 |
| Methylparaben | 0.2 |
| Smectite | 1.0 |
| Purified water | balance |
| C Perfume | 0.05 |
| Total | 100.0% |

Example 38

Ointment

An ointment having the following formulation was prepared and filled in a polypropylene jar container.

| | |
|---|---|
| Propyl gallate-3,5-diglucoside | 0.5% |
| Propyl gallate-3-glucoside | 0.04 |
| Stearyltrimethylammonium chloride | 4.0 |
| Gallic acid | 0.001 |
| Sodium sulfate | 0.001 |
| White vaseline | 40.0 |
| Cetanol | 18.0 |
| Sorbitan sesqui-oleate | 5.0 |
| Lauromacrogol | 0.5 |
| Capsicum tincture | 0.01 |
| Tanghin extract | 1.0 |
| Perfume | 0.2 |
| Purified water | balance |
| Total | 100.0% |

Example 39

Whole-Body Lotion

A whole-body lotion having the following formulation was prepared and filled in a pillow pack using an aluminum deposited film.

| | |
|---|---:|
| Gallic acid-4-maltoside | 0.5% |
| Gallic acid-3,5-diglucoside | 15.0 |
| Gallic acid-4-glucoside | 0.8 |
| Gallic acid | 0.002 |
| Sodium sulfate | 0.003 |
| Minoxidil | 1.0 |
| Monoglyceride pentadecanoate | 3.0 |
| Tocopherol acetate | 0.1 |
| Oxidized Co Enzyme A | 0.001 |
| Ellagic acid | 0.02 |
| Hinokitiol | 0.1 |
| Camphor | 0.02 |
| β-Glycyrrhizic acid | 0.5 |
| Ammonium glycyrrhizinate | 0.05 |
| Pantothenyl ethyl ether | 1.0 |
| D-Pantothenyl alcohol | 1.0 |
| Piroctone olamin | 0.05 |
| Pentaglycerine monomyristate | 1.0 |
| Sorbitan monolaurate | 0.5 |
| Sorbitan palmitate | 2.0 |
| Sodium laurylsulfate | 0.2 |
| Lauryldimethylamide oxide | 0.1 |
| Decaglyceryl myristate | 0.5 |
| Stearyltrimethylammonium chloride | 0.05 |
| Peppermint extract | 0.5 |
| Spearmint extract | 0.5 |
| Coleus extract | 1.0 |
| Plectranthus extract | 0.5 |
| Osmoin extract | 0.1 |
| Eucheuma muricatum extract | 0.1 |
| Sophorae radix extract | 0.1 |
| Succinic acid | 0.1 |
| Benzalkonium chloride | 0.02 |
| 1-Menthyl glyceryl ether | 0.1 |
| 1-Menthol | 0.3 |
| Silicone emulsion (FZ-4672, made by Nippon Unicar Co., Ltd.) | 1.0 |
| Liquid isoparaffin | 2.0 |
| Propylene glycol | 3.0 |
| Isopropyl alcohol | 5.0 |
| Ethanol | 30.0 |
| Purified water | balance |
| Total | 100.0% |

The preparations of the above Examples 19 to 39 were evaluated with respect to the stability thereof under conditions where filled in individual containers as above example 1, and the stabilities were revealed all excellent.

The invention claimed is:

1. A preparation for external use comprising a mixture of gallic acid derivatives of the following formula (I),

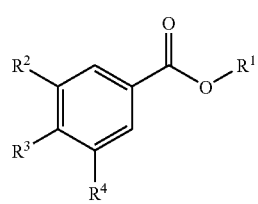

wherein $R^1$ represents a hydrogen atom, an alkali metal, an alkaline earth metal, an ammonium salt, or an alkyl or alkenyl group having from 1 to 18 carbon atoms and $R^2$, $R^3$, and $R^4$ independently represent a hydrogen atom, an hydroxyl group, an alkoxy group having from 1 to 18 carbon atoms, a polyoxyethylene group, a polyoxypropylene group, or a residue of a monosaccharide, a disaccharide, or an oligosaccharide, the mixture of gallic acid derivative of the formula (I) being composed of
   at least 95% by weight of (A) one or more gallic acid derivatives of formula (I) wherein two of $R^2$, $R^3$, and $R^4$ independently represent a residue of a monosaccharide, a disaccharide, or an oligosaccharide and
   from 0.01 wt % to less than 5 wt % of (B) one or more gallic acid derivatives of formula (I) wherein one of $R^2$, $R^3$, and $R^4$ represents a residue of a monosaccharide, a disaccharide, or an oligosaccharide,
   each weight percentage being based on the total content of the gallic acid derivatives of formula (I) in the preparation.

2. The preparation for external use according to claim 1, further comprising a cationic surface active agent.

3. The preparation for external use according to claim 1, further comprising a silicone compound.

4. A hair cosmetic comprising a preparation for external use according to claim 1 or 2 or 3.

5. The hair cosmetic of claim 4, comprising from 0.1 to 20 weight-% of a preparation according to claim 1 or 2 or 3.

* * * * *